(12) United States Patent
Skill et al.

(10) Patent No.: US 6,370,815 B1
(45) Date of Patent: Apr. 16, 2002

(54) PHOTOREACTION

(76) Inventors: Stephen Skill, Archers Water Farm, Blidworth Nottingham, England NG21 ONZ (GB); Lee Fisher Robinson, 3 Athanaeum Hall, Vale-of-Health, Hampstead, London, England NW3 1AP (GB)

( * ) Notice: Subject to any disclaimer, the term of this patent is extended or adjusted under 35 U.S.C. 154(b) by 0 days.

(21) Appl. No.: 09/529,847

(22) PCT Filed: Oct. 21, 1998

(86) PCT No.: PCT/GB98/03150

§ 371 Date: Jun. 26, 2000

§ 102(e) Date: Jun. 26, 2000

(87) PCT Pub. No.: WO99/20736

PCT Pub. Date: Apr. 29, 1999

(30) Foreign Application Priority Data

Oct. 22, 1997 (GB) ............................................. 9722351

(51) Int. Cl.⁷ ........................... C12M 3/00; A01G 31/02
(52) U.S. Cl. ..................................... 47/14; 435/298.1
(58) Field of Search ................ 47/1.4, 59, 1.01 R; 435/289.1, 298.1

(56) References Cited

U.S. PATENT DOCUMENTS

| | | | |
|---|---|---|---|
| 3,955,317 A | * 5/1976 | Gudin | ....................... 47/1.4 X |
| 4,473,970 A | 10/1984 | Hills | ............................. 47/1.4 |
| 4,489,673 A | 12/1984 | Pohlhausen | ..................... 119/2 |
| 4,868,123 A | 9/1989 | Berson et al. | |
| 5,242,827 A | 9/1993 | Chaumont et al. | .......... 435/287 |

FOREIGN PATENT DOCUMENTS

| | | |
|---|---|---|
| DE | 3520362 | 12/1986 |
| GB | 21185721 | 11/1983 |
| WO | WO 94/09113 | 4/1994 |
| WO | WO 95/06111 | 3/1995 |
| WO | WO 95/19424 | 7/1995 |
| WO | WO 96/02763 | 2/1996 |
| WO | WO 98/24879 | 6/1998 |

OTHER PUBLICATIONS

Publication by A. Vonshak, Microalgae: Laboratory Growth Techniques and the Biotechnology of Biomass Production, from Photosynthesis and Production in a Changing Environment: a field and laboratory manual, Ed. D O Hall et al., Chapter 21, pp. 338 to 355, published 1993.

* cited by examiner

*Primary Examiner*—Michael J. Carone
*Assistant Examiner*—Jeffrey L. Gellner
(74) *Attorney, Agent, or Firm*—Caesar, Rivise, Bernstein, Cohen & Pokotilow, Ltd.

(57) ABSTRACT

Photosynthetic organisms are grown in a tube having a gas inlet at one end and a gas outlet at the other. The tube containing a rotor having vanes adapted to wipe the inside surface, the tube being disposed at an angle to the horizontal in a bath containing liquid, the gas inlet being lowermost.

19 Claims, 2 Drawing Sheets

PHOTOREACTION

The invention relates to the growth of photosynthetic organisms such as microorganisms, algae, photosynthetic bacteria, photosynthetic organisms and animal symbionts; higher plant tissues, and the like.

It is one object of the invention to provide apparatus and method for the purpose specified which is particularly simple and efficient and offers other advantages.

GB-A-2118572 discloses a photosynthetic bioreactor comprising a sinuous transparent tube having a pump arranged to pump liquid culture through the tube at a ate such that a Reynolds number of 2,000 or greater is achieved. This is to ensure turbulence sufficient to ensure that all cells of the culture are frequently exposed to radiation.

U.S. Pat. No. 4,473,970 discloses an upright tubular bioreactor through which $CO_2$ and $O_2$ are pumped, above a liquid culture medium which is subjected to continuous agitation by being pumped. Transverse baffles are located in the gas flow path.

U.S. Pat. No. 5,242,827 discloses a tubular bioreactor and teaches that it is known to include circulating plastics balls in such reactors in order to ensure an agitation of the nutrient medium and cleaning of the tubes as a result of the balls rubbing on their walls. Means for the introduction and removal of the balls and for stopping their flow are disclosed.

WO-A-94/09113 discloses a tubular photobioreactor having a rectangular bore and a "ring" of rectangular cross-section which is forced through the tube for scraping its inner walls.

In one aspect the invention provides apparatus for use in growing cultures of photosynthetic organisms, the apparatus comprising a bath containing liquid, at least one elongate passageway having a gas inlet towards one end and a gas outlet towards the other; and means adapted to wipe the inside surface of the passageway; the passageway being located within the liquid at an inclination to the horizontal with a gas inlet being lowermost.

Preferably the wiping means is a rotary wiping means, preferably having a rotary axis which is substantially parallel to the longitudinal axis of the passageway.

Preferably the means for wiping the inside of the passageway is a rotor having vanes and extending the length of the passageway; and a motor or the like being present for rotating the rotor.

The passageway is suitably made of a material which is substantially transparent to visible radiation such as glass or polycarbonate. The passageway may optionally be made of an opaque material, e.g. where a dark stage is required. If appropriate the passageway may have a covering or the wall material may include photo adjusting compounds.

Preferably the passageway is disposed at an angle to the horizontal ranging from substantially vertical to say 30° or 40° to the horizontal.

Preferably the passageway is generally circular in cross-section.

The bath may for example, take the form of a lagoon, pond or the like. Preferably the bath contains water as the liquid. To enhance the photosynthetic and heating effect preferably the wall of the bath has light reflective surfaces above and/or below the level of the liquid. Dyes or fluorescent agents may optionally be present in the water to selectively remove visible, UV or IR radiation or enhance it as in fluorescence. Where the bath is located outside a building preferably means are present to reduce heat loss at night and/or to cause cooling during the day, whereby to maintain the temperature of the liquid substantially constant. Such means may for example, be a cover (which may be an integral sheet or say floating balls of polystyrene) to insulate or a fountain to circulate the water to cool it by enhanced evaporation.

In another aspect the invention provides apparatus for use in the culture of photosensitive organisms, comprising a pond or lagoon containing water, elongate containers of the organisms being present in the water, and the containers being disposed at an inclination to the horizontal.

In another aspect the invention provides an assembly comprising a plurality of passageways as defined, arranged generally parallel to each other, the passageways being free of the gas inlet and outlet, neighbouring passageways communicating through a hollow bridging element which includes the gas inlet and the gas outlet.

In yet another aspect the invention provides a method of growing a culture of micro-organisms comprising passing a culture liquid through apparatus or the assembly as defined and supplying to the gas inlet $CO_2$ gas and/or other gases which may aid growth or constituent balance of specific organisms. Oxygen or like gases are released via the outlet and may be collected. The liquid may be passed continuously or in a batch mode.

A wide variety of micro organisms may be treated in the apparatus of the invention. Examples include microalgae, macroalgae tissue, photosynthetic bacteria, photosynthetic archaebacteria, heterotophic bacteria fungi, plant tissue culture, water fleas; and the like. Apparatus of the invention may be used in the culture of micro-organisms for the production of colourings and anti-oxidants, fishfeeds, pharmaceuticals and the like.

Apparatus of the invention is able to maintain continuously growing cultures of Haematococcus for several months to provide commercial harvests of Astaxanthin. Apparatus of the invention can be used for the culture of strains of Dunaliella, a unicellular, flagellated green algae without a cell wall which contain high concentration (up to 10%) of beta-carotene when growing under high light intensities and high salinities (100 g/l). Beta-carotene has traditionally been used as a food colouring agent and may have medical uses. One major benefit of the apparatus of the invention is purity of the products. Although several companies grow Dunaliella in open ponds, product contamination regularly occurs. Apparatus of the invention is able to maintain continuously growing contaminant-free cultures of Dunaliella resulting in high purity beta-carotene.

Apparatus of the invention can be used to produce live feeds, on site, or dried and processed algae based feeds that are shipped to users.

Micro algae cultivated in the apparatus of the invention provide the most effective biological means known to remove carbon dioxide from the atmosphere. At the same time, the biomass they produce an be used as fuel.

Micro algae can remove carbon dioxide from the atmosphere 25 times faster than the fastest growing trees. Carbon dioxide is removed from stack gases before it even enters the atmosphere. Trees, on the other hand, remove carbon dioxide after it enters the earth's atmosphere. Biomass from micro algae can be used as a fuel. Micro algae produced at the site of a fossil fuel burning plant could be directly fed into the fuel combustion process.

Micro algae cultivated in accordance with the invention can supply quantities adequate for all purposes ranging from screening to production.

Apparatus of the invention may also be used in the treatment of gases.

Further preferred features are defined in the dependent claims.

In order that the invention may be well understood it will now be described by way of example with reference to the accompanying diagrammatic drawings, in which FIG. 1 is a side elevation partly in section of an arrangement incorporating an apparatus of the invention;

Figure 1:
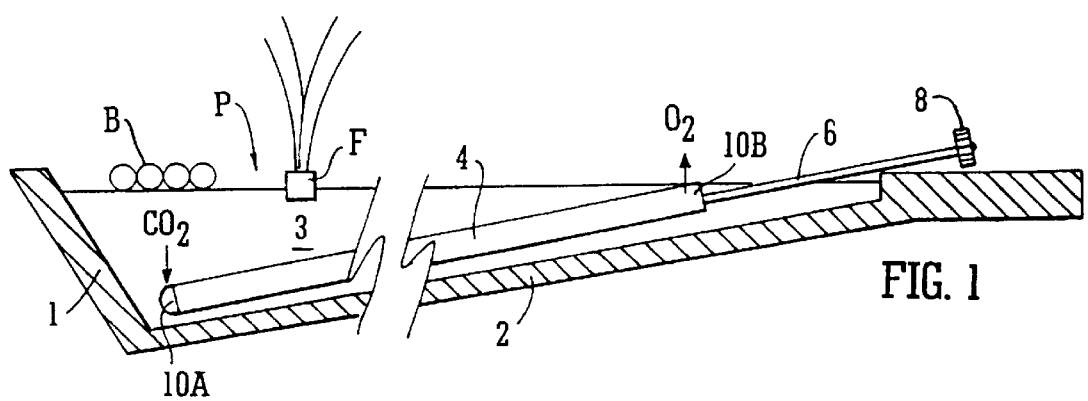
Figure 2:
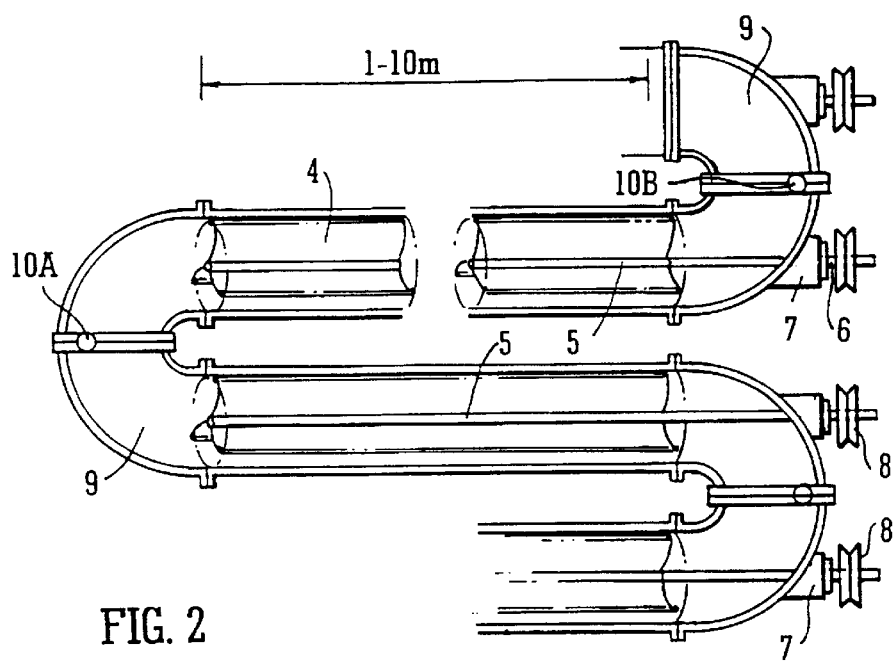
FIG. 2 is a plan view of part of the apparatus of FIG. 1.

The pond P shown in FIG. 1 comprises a concrete or like wall 1 having a sloping floor 2. The pond contains water 3. An assembly A of parallel pipes or passageways 4 is located in the water. Each contains a rotor 5 connected to a shaft 6 and via a bearing and seal 7 to a drive wheel 8 located on an edge of the pond P. For the sake of clarity the diameter of the passageways 4 is shown greatly exaggerated in relation to their length. As shown in FIG. 2, neighbouring passageways 4 are joined together by U-shaped connectors 9 so that a continuous serpentine assembly is formed. One passageway 4 is shown cut away in the middle purely to illustrate the cross-section of one rotor assembly. Each connector incorporates a port, 10A at the lower end acting as a gas inlet port and the upper one, 10B, located at or above the level of the water acting as a gas release vent. The ports may be valved. The passageways may, for example, range from 1 to 50 metres in length and from 50 to 1000 mm in diameter. (These dimensions are not critical.) The passageways can be made of glass or transparent plastics for example. The passageways extend downwardly at an angle of about 30° to about 40° from the horizontal, being held in a framework, not shown. Optionally a cover in the form of floating polystyrene balls B is provided to ensure heat retention at night. The cover is normally removed during the day.

A fountain F is provided to cool the water if necessary.

Figure 3:
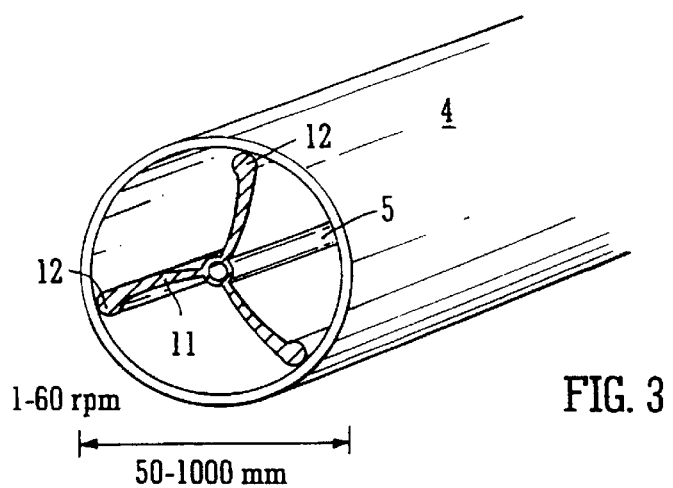
FIG. 3 is an enlarged perspective view of a rotor in one passageway.
Figure 4:
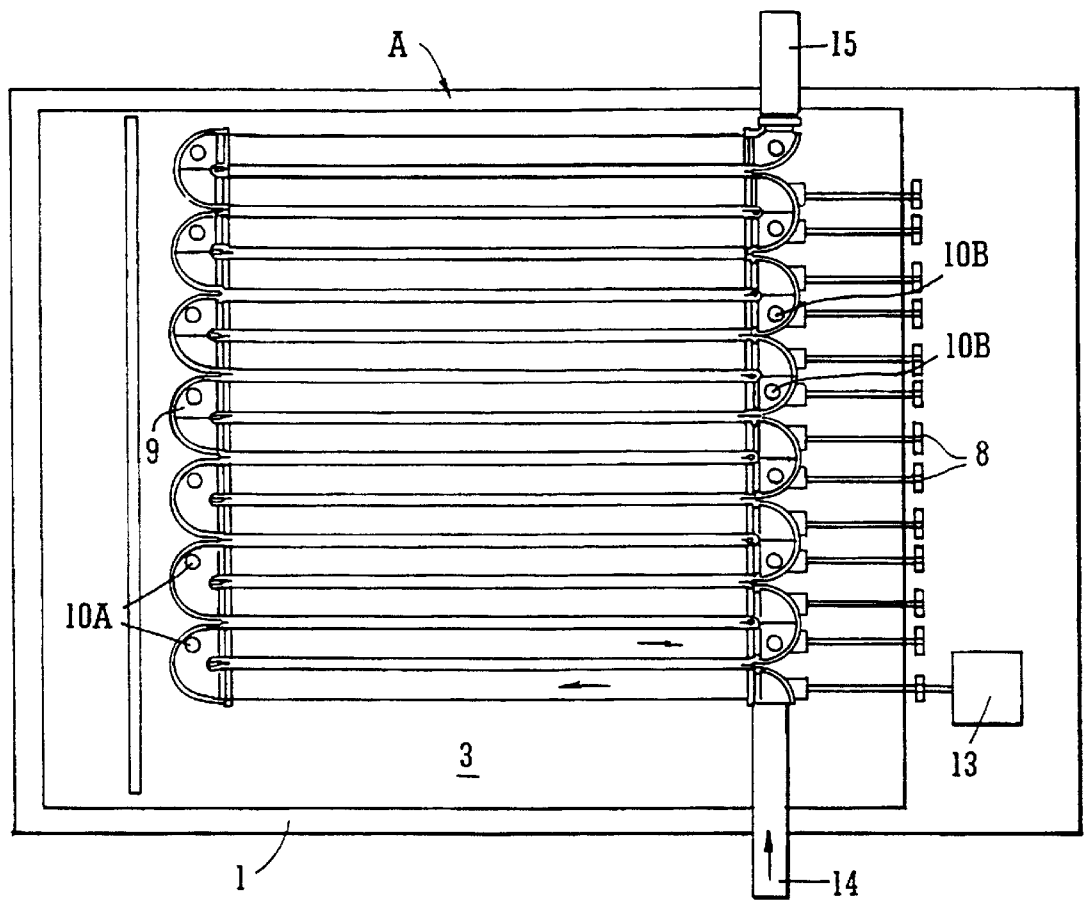
FIG. 4 is a plan view of one assembly.

Three vanes 11 are equally angularly spaced about the rotor 5 along the length thereof, as best seen in FIGS. 2 and 3. The vanes are made of a flexible material such as a natural or synthetic rubber and have expanded or bulbous free edges 12. In use the vanes act as cleaning blades to wipe the inner surface of the passageways and also act as an agitator and a stirrer for the mixing of gases. It is simple to remove the rotor, e.g. to clean both the rotor and the inner surface of the passageway.

A motor 13 is connected to a drive coupling chain or belt (not shown) to drive the drive wheels 8. The motor is arranged to rotate the rotors 5 at from about 1 to about 60 rpm. In use, $CO_2$ or other gas mixtures are introduced into the inlets 10A, and a liquid medium containing photoorganism or inocula is introduced via a major inlet 14 and passed through the assembly A. Depending on the ambient temperature and prevailing weather conditions the surface of the water is exposed to sunlight. For example, in the case of high sunlight the water is agitated to improve evaporative cooling. At night the surface may be covered to conserve heat, the intention being to maintain the water temperature at the optimum for biomass growth. Gases such as oxygen or hydrogen are vented via the outlets 10B and may be collected. The biomass may be removed via the exit 15 for further processing as appropriate.

The surfaces of the wall 1 may be coated with reflective paint. The water absorbs UV which reduces damage to passageways made of plastics.

The apparatus of the invention is of low cost and robust. Because it is closed to the atmosphere it allows axenic culture. The apparatus is self cleaning, simple and has efficient temperature control. The gentle agitation is ideal for delicate cells and water fleas and the like; and gas venting via the port 10B, prevents conditions such as photooxidation due to high oxygen concentrations if produced by the biomass. The operation may be plug flow or multistage. For example, the apparatus may comprise one serpentine set of passageways in a first pond held at a controlled first temperature and leading to a second set in a second pond at a second temperature. The biomass production could be optimised in the first pond and secondary metabolite production could be maximised in the second pond. The apparatus may be adapted for use with non-photosynthetic organisms, in which case the passageways will have opaque walls.

What is claimed is:

1. An apparatus for use in growing a culture of photosensitive organisms, the apparatus comprising:
   a) a bath containing culture liquid;
   b) at least one elongate passageway member in the liquid and inclined to the horizontal, the passageway member having an inside surface, a gas inlet and a gas outlet, the gas inlet being longitudinally spaced apart from the gas outlet and disposed below the gas outlet; and
   c) a rotary wiping means for wiping said inside surface of the passageway member.

2. An apparatus according to claim 1, wherein said rotary wiping means comprises a rotor disposed within and extending longitudinally with respect to the passageway member, the rotor having vanes for wiping said inside surface and the apparatus having rotary drive means for rotating said rotor.

3. An apparatus according to claim 2, wherein said vanes are flexible.

4. An apparatus according to claim 1, wherein the passageway member has a bore which is generally circular in cross-section.

5. An apparatus according to claim 1, wherein said liquid contains an agent selected from the group consisting of dyes and fluorescent agents.

6. An apparatus according to claim 1, wherein said bath has light-reflective surfaces for enhancing heating and photosynthesis.

7. An apparatus according to claim 1, wherein the passageway member is inclined at about 30° to 40° to the horizontal.

8. An apparatus according to clam 1, wherein said bath incorporates heat control means for maintaining the temperature of the liquid substantially constant, said heat control means being selected from the group consisting of means for reducing heat loss at night and means for cooling the liquid during the day.

9. An apparatus for use in the culture of photosensitive organisms, said apparatus comprising:
   a) pond means containing water;
   b) elongate containers arranged for housing the photosensitive organisms, said elongate containers being disposed at an inclination to the horizontal in the water, the elongate containers having an interior surface arranged for contacting the photosensitive organisms; and
   c) rotary wiping means for wiping said interior surface.

10. An apparatus according to claim 9, including a cover for converting the water to maintain the temperature thereof.

11. An apparatus according to claim 9, further comprising means for agitating the water to enhance evaporation.

12. An apparatus according to claim 9, further comprising means for introducing gas into said elongate containers.

13. An apparatus according to claim 9, further comprising means for releasing gas from said elongate containers.

14. An apparatus according to claim 9, said elongate containers having walls which are substantially transparent to visible light.

15. An apparatus according to claim 9, wherein said elongate containers have opaque walls.

16. A method of growing cultures of micro-organisms comprising passing a culture liquid through apparatus according to claim 1, and supplying $CO_2$ gas to the gas inlet.

17. A method according to claim 16, wherein said rotary wiping means comprises a rotor which is rotated at about 1 to 60 rpm.

18. A method according to claim 16, including the step of collecting gas from said gas outlet.

19. A method according to claim 18, wherein the microorgansims are selected from the group consisting of oxygen-generating and hydrogen-generating microorganisms.

* * * * *